United States Patent [19]

Kropp et al.

[11] 4,268,445
[45] May 19, 1981

[54] PREPARATION OF BICYCLIC ENOL-ETHERS, AND NOVEL ETHERS OF 2-(3-HYDROXYPROP-L-YL)-CYCLOALKANONES

[75] Inventors: Rudolf Kropp, Limburgerhof; Frank Thoemel, Weinheim; Axel Nuerrenbach, Gruenstadt; Werner Hoffman, Neuhofen; Franz Wenisch, Frankenthal; Hartwig Fuchs, Ludwigshafen, all of Fed. Rep. of Germany

[73] Assignee: BASF Aktiengesellschaft, Fed. Rep. of Germany

[21] Appl. No.: 117,128

[22] Filed: Jan. 31, 1980

[30] Foreign Application Priority Data

Feb. 19, 1979 [DE] Fed. Rep. of Germany ....... 2906296

[51] Int. Cl.³ ................... C07D 311/44; C07D 311/94
[52] U.S. Cl. ......................... 260/345.2; 260/345.9 R; 260/347.8; 568/347; 568/375; 568/376; 568/379
[58] Field of Search .......... 260/345.2, 345.5, 345.9 R, 260/347.8, 586 C; 568/347

[56] References Cited

U.S. PATENT DOCUMENTS 3,856,815  12/1974  Hopp et al. ........................ 260/333
3,907,831   9/1975  Becker .............................. 260/345.2

FOREIGN PATENT DOCUMENTS 2136496  8/1976  Fed. Rep. of Germany ...... 260/333

OTHER PUBLICATIONS

Nikishin et al., Bulletin of the Academy of Sciences, 9, 1924 (1961).

Primary Examiner—Nicky Chan
Attorney, Agent, or Firm—Keil & Witherspoon

[57] ABSTRACT

The preparation of bicyclic enol-ethers (I)

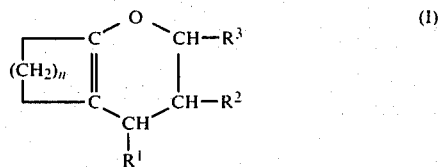

(where n is from 3 to 12, and $R^1$, $R^2$ and $R^3$ may be H or $C_1$—$C_4$-alkyl) by free radical adduct formation of $CHR^1=CR^2-CHR^3-O-R^4$ (III)(where $R^4$ is tert.-butyl, tetrahydrofuran-2-yl or tetrahydropyran-2-yl) with a cyclic ketone (IV)

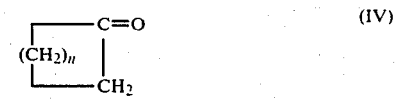

followed by acid-catalyzed cyclization, and novel compounds II

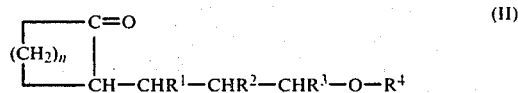

The compounds (I) and (II) are intermediates for the synthesis of musk-like fragrances.

1 Claim, No Drawings

PREPARATION OF BICYCLIC ENOL-ETHERS, AND NOVEL ETHERS OF 2-(3-HYDROXYPROP-1-YL)-CYCLOALKANONES

The present invention relates to an improved process for the preparation of bicyclic enol-ethers of the general formula I

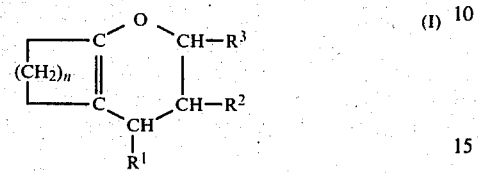

where n is from 3 to 12 and $R^1$, $R^2$ and $R^3$ are hydrogen or $C_1$—$C_4$-alkyl. The invention further relates to novel ethers of 2-(3-hydroxyprop-1-yl)-cycloalkanes, of the general formula II

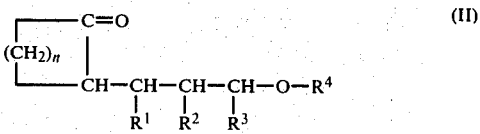

where $R^4$ is tert.-butyl, tetrahydrofuran-2-yl or tetrahydropyran-2-yl.

German Pat. No. 2,136,496 discloses the preparation of compounds (I), which are important intermediates for the synthesis of musk-like fragrances, by free radical adduct formation of an allyl alcohol or an allyl ester (III')

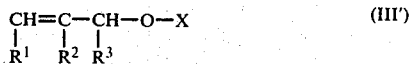

where X is H or -CO-alkyl, with a cyclic ketone (IV)

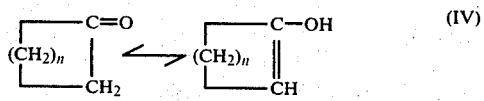

followed by acid-catalyzed cyclization of the resulting adduct (II')

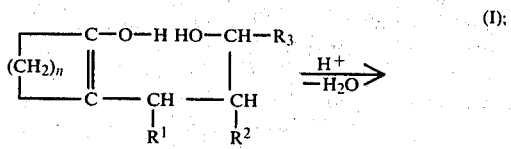

where allyl esters are used, the acid radical must, before cyclization, be removed hydrolytically.

This process has the disadvantage that allyl alcohol and its homologs are very sensitive compounds. Conversely, if esters of these alcohols are used, an additional process step, ie. hydrolytic removal of the acid, must be carried out after the adduct formation.

Further, Isvest. Akad. Nauk, SSSR, Otdel. Khim. Nauk (1961), page 2065 f discloses the free radical α-adduct formation of allyl ethers of n-alkan-1-ols with cyclopentanone and cyclohexanone to give compounds of type (II), but these compounds cannot be cyclized to give bicyclic enol-ethers.

It is an object of the present invention to improve the process known in principle from German Pat. No. 2,136,496 so as to avoid the stated disadvantages.

We have found that this object is achieved and that bicyclic enol-ethers of the general formula (I)

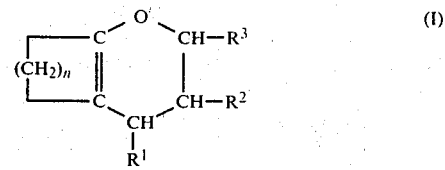

where n is from 3 to 12 and $R^1$, $R^2$ and $R^3$ are hydrogen or $C_1$-$C_4$-alkyl, are obtained in an advantageous manner by free radical adduct formation of an allyl compound with a cyclic ketone of the general formula (IV)

followed by acid-catalyzed cyclization to give (I), if the allyl compound used is an allyl ether of the general formula III

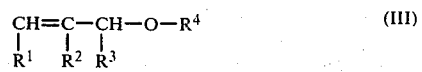

where $R^4$ is tert.-butyl, tetrahydrofuran-2-yl or tetrahydropyran-2-yl.

In accordance with the principally desired products (I), the starting compounds (III) are in particular derived from allyl alcohol. In addition, those derived from but-2-en-1-ol, but-1-en-3-ol and methallyl alcohol are of particular importance.

The ethers, as defined above, of these alcohols may be obtained in a simple manner by reacting the alcohols with isobutene, 2,3-dihydrofuran or 2,3-dihydropyran in the presence of an acid catalyst, particularly advantageously an acid ion exchanger. This etherification is in general carried out under atmospheric or superatmospheric pressure, up to about 50 bar, and at from 0° to 100° C., preferably from 40° to 80° C.

Amongst the starting compounds (IV), cyclopentanone, cyclohexanone, cyclooctanone and especially cyclododecanone deserve particular mention.

In principle, any free radical catalyst can be used for the reaction of (III) with (IV), but preferred catalysts are those which only become active, ie. decompose into free radicals, at temperatures at which the α-adduct formation of (III) with (IV) takes place at a sufficiently high rate. These temperatures are as a rule from 80° to 180° C., especially from 120° to 150° C. In general terms, the reaction can be carried out at from 50° to 200° C., though the rate drops substantially below 80° C. whilst above 150° C. increased formation of by-products must as a rule be expected. In selecting the temperature, a further important factor is that the reaction should if possible be carried out under atmospheric pressure since either reduced pressure—eg. down to about 200 mbar absolute pressure—or superatmospheric pressure—eg. up to about 50 bar—entails the economic disadvantage that pressure equipment must be used.

For the reasons mentioned, suitable catalysts for the particularly preferred temperature range of from 120° to 150° C. are, for exampe, dibenzoyl peroxide, tert.-butyl peroctoate, azodiisobutyronitrile and especially di-tert.-butyl peroxide.

(III) and (IV) react with one another in the equimolar ratio, but to suppress side reactions it is in general advantageous to employ (IV) in up to about 20-fold molar excess. The amount of free radical catalyst is preferably from 0.05 to 0.7 mole, especially from 0.1 to 0.3 mole, per mole of (III).

If (III) and (IV) are liquid at the reaction temperature and the catalyst is sufficently soluble in the reaction mixture, the use of an inert solvent is as a rule unnecessary. If it is nevertheless desired to use a solvent, for example because the starting compound is available in the form of a solution, or because the formation of by-products can at times be reduced by using solvents, suitable solvents are, for example, petroleum ether, cyclohexane, benzene and chlorobenzene.

The reaction of (III) with (IV) gives the compounds (II)

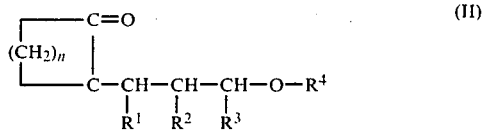

which can, if desired, be isolated in a conventional manner, but which are preferably directly subjected to the acid-catalyzed cyclization reaction, which proceeds with elimination of water and of isobutene, 2,3-dihydrofuran or 2,3-dihydropyran.

In principle, any acid, ie. both proton acids and Lewis acids, may be used, in either a homogeneous or a heterogeneous phase (so that, for example, acid ion exchangers can also be employed). For technological reasons, however, strong organic acids of low volatility, used in a homogeneous phase, have proved particularly suitable, p-toluenesulfonic acid, a cheap product, being especially preferred.

The amount of acid is advantageously from 0.001 to 0.3, especially from 0.05 to 0.2, mole equivalent per mole of (II).

The cyclization is preferably carried out at from 60° to 150° C., especially from 80° to 130° C., under a pressure of from 0.05 mbar to 50 bar, especially from 0.1 to 1 mbar. The removal of the water can be assisted by continuous azeotropic distillation, for example with toluene. After separating off the water, the olefinic cleavage products can be recycled to the stage in which (III) is prepared.

The process can be carried out either batchwise or continuously, by the conventional techniques apart from the improvement according to the invention, so that further description is unnecessary. Similar remarks apply to the working up of the products (I).

The process especially offers the advantage that the allyl alcohol (III') is converted at a relatively low temperature to the ether (III), which is substantially easier to handle than the free alcohol at the temperature at which the free radical adduct formation is carried out. In spite of the additional etherification stage, the process proves to be more economical than if the alcohol (III') is used directly.

EXAMPLE 1

Preparation of 13-oxabicyclo-[10.4.0]-hexadec-Δ-1,12-ene.

A solution of 114 g (1 mole) of allyl tert.-butyl ether and 29.2 g (0.2 mole) of di-tert.-butyl peroxide was added in the course of 4 hours to 1,820 g (10 moles) of cyclododecanone at 140° C., under a nitrogen atmosphere, and the mixture was kept at the same temperature for a further hour. The excess cyclododecanone was then distilled off, after which the residue was heated with 10 g (58 millimoles) of p-toluenesulfonic acid for one hour at 130° C. under 300 mbar. This resulted in the elimination of 0.7 mole of water and 0.7 mole of isobutene. Conventional working up gave the above compound in 56% yield.

Boiling point 112°–114° C./0.1 mbar; $n_D^{20} = 1.5079$.

EXAMPLE 2

Preparation of 13-oxabicyclo-[10.4.0]-hexadec-Δ-1,12-ene.

Cyclododecanone and allyl tert.-butyl ether were reacted with one another over 6 hours, by a method similar to that of Example 1. After removing the excess cyclododecanone, the residue was refluxed with 10 g of p-toluenesulfonic acid in 1 liter of toluene under atmospheric pressure for 3 hours, with continuous azeotropic distillation of the water. The solution was then washed neutral with dilute aqueous $NaHCO_3$ solution, and worked up in a conventional manner. The yield of the product shown in the title was 65%.

EXAMPLE 3

2-(3-tert.-Butoxy-prop-1-yl)-cyclopentanone

A solution of 87 g (0.76 mole) of allyl tert.-butyl ether and 33 g (0.23 mole) of di-tert.-butyl peroxide was added over 4 hours to 638 g (7.6 moles) of cyclopentanone at 125°–130° C., under a nitrogen atmosphere, and the mixture was then kept at 120° C. for 4 hours.

Working up the reaction mixture by distillation gave 2-(3-tert.-butoxy-prop-1-yl)-cyclopentanone in 50% yield.

Boiling point 95°–90° C./0.4 mbar; $n_D^{24.5} = 1.4517$.

EXAMPLE 4

Preparation of 6-oxabicyclo-[3.4.0]-non-Δ-1,5-ene 37 g (0.19 mole) of the product from Example 3 and 5 g (29 millimoles) of p-toluenesulfonic acid were heated for 1 hour at 100° C. under 18 mbar. The reaction mixture was then worked up in a conventional manner; the yield of the bicyclic enol-ether shown in the title was 30%, based on allyl ether employed.

Boiling point 68°–70° C./0.15 mbar.

EXAMPLE 5

2-(3-tert.-Butoxy-prop-1-yl)-cyclohexanone

A solution of 114 g (1 mole) of allyl tert.-butyl ether and 29.2 g (0.2 mole) of di-tert.-butyl peroxide was added over 2 hours to 980 g (10 moles) of cyclohexanone at 140° C., while stirring, and the mixture was then kept at the same temperature for a further hour. Working up the reaction mixture by distillation gave 2-(3-tert-butoxy-prop-1-yl)-cyclohexanone in 60% yield.

Boiling point 85°–90° C./0.05 mbar; $n_D^{24.5} = 1.4553$.

EXAMPLE 6

Preparation of 7-oxabicyclo-[4.4.0]-dec-Δ-1,5-ene 180 g (0.85 mole) of the product from Example 5 were cyclized in the presence of 10 g (58 millimoles) of p-toluenesulfonic acid in 1 liter of toluene by a method similar to that of Example 2. The yield of the product shown in the title was 42%, based on the allyl ether.

Boiling point 66°–70° C./0.05 mbar; $n_D^{24.5}=1.4932$.

EXAMPLE 7

2-(3-tert.-Butoxy-prop-1-yl)-cyclooctanone 504 g (4 moles) of cyclooctanone, 46 g (0.4 mole) of allyl tert.-butyl ether and 23 g (0.16 mole) of di-tert.-butyl peroxide were reacted as described in Example 1. The yield of 2-(3-tert.-butoxy-prop-1-yl)-cyclooctanone was 84%.

Boiling point 105°–110° C./0.15 mbar; $n_D^{24.5}=1.4681$.

EXAMPLE 8

Preparation of 9-oxabicyclo-[6.4.0]-dodec-Δ-1,8-ene 49 g (0.2 mole) of the product from Example 7 were cyclized in the presence of 5 g (29 millimoles) of p-toluenesulfonic acid in 0.5 liter of toluene by a method similar to that of Example 2. Working up gave the compound shown in the title in 75% yield, based on the allyl ether.

Boiling point 55° C./0.15 mbar; $n_D^{24.5}=1.4938$.

EXAMPLE 9

Preparation of 13-oxabicyclo-[10.4.0]-hexadec-Δ-1,12-ene 142 g (1 mole) of 2-allyloxytetrahydropyran and 56 g (0.38 mole) of di-tert.-butyl peroxide were added over 6 hours to 237 g (1.3 moles) of cyclododecanone at 140° C., and the mixture was then kept at the same temperature for a further 5 hours.

After removing the excess cyclododecanone, the adduct was heated with 1 g (6 millimoles) of p-toluenesulfonic acid at 125° C. under 0.1 mbar, whereupon the compound shown in the title distilled and was obtained in 65% yield.

If 10 moles of cyclododecanone were used under otherwise identical conditions, the yield was increased to 75%.

EXAMPLE 10

Preparation of 7-oxabicyclo-[4.4.0]-dec-Δ-1,6-ene 980 g (10 moles) of cyclohexanone, 142 g (1 mole) of 2-(allyloxy)-tetrahydropyran and 56 g (0.38 mole) of di-tert.-butyl peroxide were reacted, by a method similar to that of Example 6, to give the compound shown in the title; the yield was 55%.

EXAMPLE 11

Preparation of 14-methyl-13-oxabicyclo-[10.4.0]-hexadec-Δ-1,12-ene 910 g (5 moles) of cyclododecanone, 78 g (0.5 mole) of 2-(but-1-en-3-yloxy)-tetrahydropyran and 28 g (0.18 mole) of di-tert.-butyl peroxide were reacted, by a method similar to that of Example 6, to give the compound shown in the title. The yield was 44%.

Boiling point 110°–112° C./0.1 mbar.

EXAMPLE 12

Preparation of 13-oxabicyclo-[10.4.0]-hexadec-Δ-1,12-ene

A solution of 57 g (0.5 mole) of allyl tert.-butyl ether and 23 g (0.1 mole) of tert.-butyl peroctoate was added over 4 hours to 455 g (2.5 moles) of cyclododecanone at 100° C., under a nitrogen atmosphere, and the mixture was then kept at the same temperature for a further hour. The excess cyclododecanone was then distilled off, after which the residue was heated with 3 g (17.4 millimoles) of p-toluenesulfonic acid for one hour at 100° C. under 20 mbar. The reaction mixture was then worked up in a conventional manner; the yield of the bicyclic enol-ether shown in the title was 30%, based on allyl ether.

EXAMPLE 13

Continuous preparation of 13-oxabicyclo-[10.4.0]-hexadec-Δ-1,12-ene

A solution of 1,400 g of cyclohexane, 310 g (5 moles) of cyclododecanone, 114 g (1 mole) of allyl tert.-butyl ether and 58.4 g (0.4 mole) of di-tert.-butyl peroxide was pumped, over 25 hours, through an 0.3 liter stirred autoclave at 150° C. under 18 bar. The solvent and excess cyclododecanone were distilled from the discharged material, after which the residue was heated with 15 g (87 millimoles) of p-toluenesulfonic acid for one hour at 120° C. under 300 mbar. Working up in a conventional manner gave the compound shown in the title in 40% yield.

We claim:

1. A process for the preparation of a bicyclic enol-ether of the general formula (I)

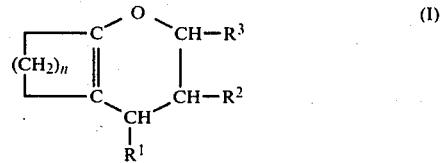

where n is from 3 to 12 and $R^1$, $R^2$ and $R^3$ are hydrogen or $C_1$-$C_4$-alkyl, by free radical adduct formation of an allyl compound with a cyclic ketone of the general formula (IV)

and subsequent acid-catalyzed cyclization to give (I), wherein the allyl compound used is an allyl ether of the general formula (III)

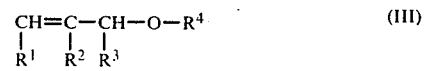

where $R^4$ is tert.-butyl, tetrahydrofuran-2-yl or tetrahydropyran-2-yl.

* * * * *